United States Patent
Snow et al.

(10) Patent No.: US 8,725,435 B2
(45) Date of Patent: May 13, 2014

(54) SYRINGE-BASED LEAK DETECTION SYSTEM

(75) Inventors: Sean Snow, Carpinteria, CA (US); Mark O'Donnell, Goleta, CA (US); Amy Tezel, Goleta, CA (US); Marcos Borrell, Goleta, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 313 days.

(21) Appl. No.: 13/085,906

(22) Filed: Apr. 13, 2011

(65) Prior Publication Data
US 2012/0265456 A1  Oct. 18, 2012

(51) Int. Cl.
| G01M 3/04 | (2006.01) |
| G06F 19/00 | (2011.01) |
| A61F 5/00 | (2006.01) |
| G01M 3/26 | (2006.01) |

(52) U.S. Cl.
CPC .............. *A61F 5/0056* (2013.01); *G01M 3/04* (2013.01); *G01M 3/26* (2013.01); *A61F 2005/002* (2013.01)
USPC ................... 702/51; 600/37; 702/47; 702/50

(58) Field of Classification Search
CPC .. A61F 5/0056; A61F 2005/002; G01M 3/04; G01M 3/26
USPC ............ 702/47, 50, 51, 55, 67, 98; 128/861, 128/899; 600/30, 37; 606/157, 192
See application file for complete search history.

(56) References Cited

U.S. PATENT DOCUMENTS

| 2,163,048 A | 6/1939 | McKee |
| 3,667,081 A | 6/1972 | Burger |
| 3,840,018 A | 10/1974 | Heifetz |
| 4,117,727 A | 10/1978 | Friswell et al. |
| 4,118,805 A | 10/1978 | Reimels |
| 4,157,713 A | 6/1979 | Clarey |
| 4,286,584 A | 9/1981 | Sampson et al. |
| 4,370,982 A | 2/1983 | Reilly |
| 4,592,339 A | 6/1986 | Kuzmak et al. |
| 4,592,355 A | 6/1986 | Antebi |
| 4,601,713 A | 7/1986 | Fuqua |
| 4,603,699 A | 8/1986 | Himpens |
| 4,696,288 A | 9/1987 | Kuzmak et al. |
| 4,760,837 A | 8/1988 | Petit |
| 4,858,619 A | 8/1989 | Toth |

(Continued)

FOREIGN PATENT DOCUMENTS

| CN | 1250382 | 4/2000 |
| CN | 1367670 | 9/2002 |

(Continued)

OTHER PUBLICATIONS

Bio Enterics Lap-Band Adjustable Gastric Banding System, Inamed Health, pub. 18007 Aug. 28, 2003, pp. 1-115.

*Primary Examiner* — John H Le
(74) *Attorney, Agent, or Firm* — Gordon & Jacobson, PC

(57) ABSTRACT

Generally described herein are devices, methods and systems related to detecting a leak present in a gastric banding system for the treatment of obesity. For example, a leak detector may include a syringe, a leak sensing unit and a needle, and may measure a pressure decay within a gastric banding system after the needle penetrates the patient's skin and is inserted into an access port connected to the gastric band of the gastric banding system. The pressure decay may be interpreted to determine if a leak is present in the gastric banding system.

21 Claims, 7 Drawing Sheets

(56) References Cited

U.S. PATENT DOCUMENTS

| | | |
|---|---|---|
| 4,872,483 A | 10/1989 | Shah |
| 4,881,939 A | 11/1989 | Newman |
| 4,919,650 A | 4/1990 | Feingold et al. |
| 4,989,756 A | 2/1991 | Kagamihara et al. |
| 5,074,868 A | 12/1991 | Kuzmak |
| 5,120,313 A | 6/1992 | Elftman |
| 5,160,338 A | 11/1992 | Vincent |
| 5,226,429 A | 7/1993 | Kuzmak |
| 5,259,399 A | 11/1993 | Brown |
| 5,277,333 A | 1/1994 | Shimano |
| 5,318,533 A | 6/1994 | Adams et al. |
| 5,383,858 A | 1/1995 | Reilly et al. |
| 5,425,716 A | 6/1995 | Kawasaki et al. |
| 5,449,368 A | 9/1995 | Kuzmak |
| 5,496,313 A | 3/1996 | Gentelia et al. |
| 5,569,839 A | 10/1996 | Ajot et al. |
| 5,601,604 A | 2/1997 | Vincent |
| 5,649,546 A | 7/1997 | Steinbeck |
| 5,658,298 A | 8/1997 | Vincent et al. |
| 5,681,284 A | 10/1997 | Herskowitz |
| 5,741,232 A | 4/1998 | Reilly et al. |
| 5,748,200 A | 5/1998 | Funahashi |
| 5,758,667 A | 6/1998 | Slettenmark |
| 5,795,333 A | 8/1998 | Reilly et al. |
| 5,808,203 A | 9/1998 | Nolan, Jr. et al. |
| RE36,176 E | 3/1999 | Kuzmak |
| 5,891,089 A | 4/1999 | Katz et al. |
| 5,910,149 A | 6/1999 | Kuzmak |
| 5,938,669 A | 8/1999 | Klaiber et al. |
| 5,997,502 A | 12/1999 | Reilly et al. |
| 6,010,511 A | 1/2000 | Murphy |
| 6,074,341 A | 6/2000 | Anderson et al. |
| 6,090,064 A | 7/2000 | Reilly et al. |
| 6,102,678 A | 8/2000 | Peclat |
| 6,102,922 A | 8/2000 | Jakobsson et al. |
| 6,117,086 A | 9/2000 | Shulze |
| 6,129,668 A | 10/2000 | Haynor et al. |
| 6,179,569 B1 | 1/2001 | Kojima et al. |
| 6,210,347 B1 | 4/2001 | Forsell |
| 6,221,024 B1 | 4/2001 | Miesel |
| 6,306,116 B1 | 10/2001 | Hancock |
| 6,371,942 B1 | 4/2002 | Schwartz et al. |
| 6,402,717 B1 | 6/2002 | Reilly et al. |
| 6,402,718 B1 | 6/2002 | Reilly et al. |
| 6,432,040 B1 | 8/2002 | Meah |
| 6,453,907 B1 | 9/2002 | Forsell |
| 6,454,699 B1 | 9/2002 | Forsell |
| 6,461,293 B1 | 10/2002 | Forsell |
| 6,464,628 B1 | 10/2002 | Forsell |
| 6,470,892 B1 | 10/2002 | Forsell |
| 6,475,136 B1 | 11/2002 | Forsell |
| 6,475,192 B1 | 11/2002 | Reilly et al. |
| 6,511,490 B2 | 1/2003 | Robert |
| 6,547,801 B1 | 4/2003 | Dargent et al. |
| 6,562,008 B1 | 5/2003 | Reilly et al. |
| 6,579,301 B1 | 6/2003 | Bales et al. |
| 6,635,020 B2 | 10/2003 | Tripp, Jr. et al. |
| 6,638,258 B2 | 10/2003 | Schwartz et al. |
| 6,676,674 B1 | 1/2004 | Dudai |
| 6,691,047 B1 | 2/2004 | Fredericks |
| 6,725,726 B1 | 4/2004 | Adolfs et al. |
| 6,733,478 B2 | 5/2004 | Reilly et al. |
| 6,778,927 B2 | 8/2004 | Cha et al. |
| 6,799,698 B2 | 10/2004 | Ono et al. |
| 6,808,513 B2 | 10/2004 | Reilly et al. |
| 6,966,875 B1 | 11/2005 | Longobardi |
| 7,027,935 B2 | 4/2006 | Shimase et al. |
| 7,037,344 B2 | 5/2006 | Kagan et al. |
| 7,044,933 B2 | 5/2006 | VanDiver et al. |
| 7,060,080 B2 | 6/2006 | Bachmann |
| 7,118,526 B2 | 10/2006 | Egle |
| 7,128,750 B1 | 10/2006 | Stergiopulos |
| 7,195,610 B1 | 3/2007 | Flachbart |
| 7,238,191 B2 | 7/2007 | Bachmann |
| 7,282,023 B2 | 10/2007 | Frering |
| 7,288,064 B2 | 10/2007 | Boustani et al. |
| 7,310,557 B2 | 12/2007 | Mashino et al. |
| 7,311,716 B2 | 12/2007 | Byrum |
| 7,311,717 B2 | 12/2007 | Egle |
| 7,314,443 B2 | 1/2008 | Jordan et al. |
| 7,314,598 B2 | 1/2008 | Nishino |
| 7,338,433 B2 | 3/2008 | Coe |
| 7,351,198 B2 | 4/2008 | Byrum et al. |
| 7,364,542 B2 | 4/2008 | Jambor et al. |
| 7,367,937 B2 | 5/2008 | Jambor et al. |
| 7,416,528 B2 | 8/2008 | Crawford et al. |
| 7,481,763 B2 | 1/2009 | Hassler, Jr. et al. |
| 7,500,944 B2 | 3/2009 | Byrum et al. |
| 7,507,221 B2 | 3/2009 | Neer |
| 7,530,943 B2 | 5/2009 | Lechner |
| 7,585,280 B2 | 9/2009 | Wilson et al. |
| 7,594,885 B2 | 9/2009 | Byrum |
| 7,601,162 B2 | 10/2009 | Hassle, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,699,770 B2 | 4/2010 | Hassler, Jr. et al. |
| 7,727,141 B2 | 6/2010 | Hassler, Jr. et al. |
| 7,758,493 B2 | 7/2010 | Gingras |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,794,386 B2 | 9/2010 | Brooks |
| 7,811,298 B2 | 10/2010 | Birk |
| 7,927,270 B2 | 4/2011 | Dlugos et al. |
| 2001/0011543 A1 | 8/2001 | Forsell |
| 2002/0038105 A1 | 3/2002 | Schwartz et al. |
| 2002/0095181 A1 | 7/2002 | Beyar |
| 2002/0123716 A1 | 9/2002 | VanDiver et al. |
| 2002/0133081 A1 | 9/2002 | Ackerman et al. |
| 2002/0139208 A1 | 10/2002 | Yatskov |
| 2002/0152816 A1 | 10/2002 | Kim |
| 2002/0177811 A1 | 11/2002 | Reilly et al. |
| 2002/0198548 A1 | 12/2002 | Robert |
| 2003/0009123 A1 | 1/2003 | Brugger |
| 2003/0045775 A1 | 3/2003 | Forsell |
| 2003/0060754 A1 | 3/2003 | Reilly et al. |
| 2003/0073880 A1 | 4/2003 | Polsky et al. |
| 2003/0167022 A1 | 9/2003 | Dijkman |
| 2003/0171887 A1 | 9/2003 | Cha et al. |
| 2003/0208212 A1 | 11/2003 | Cigaina |
| 2003/0213285 A1 | 11/2003 | Wheeler et al. |
| 2004/0034479 A1 | 2/2004 | Shimase et al. |
| 2004/0069714 A1 | 4/2004 | Ferguson |
| 2004/0153106 A1 | 8/2004 | Dudai |
| 2004/0171942 A1 | 9/2004 | Ackerman et al. |
| 2004/0230137 A1 | 11/2004 | Mouton |
| 2004/0235025 A1 | 11/2004 | Mori et al. |
| 2004/0243057 A1 | 12/2004 | Vinten-Johansen |
| 2004/0254533 A1 | 12/2004 | Schriver et al. |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0070934 A1 | 3/2005 | Tanaka et al. |
| 2005/0070937 A1 | 3/2005 | Jambor et al. |
| 2005/0119672 A1 | 6/2005 | Benchetrit |
| 2005/0131383 A1 | 6/2005 | Chen et al. |
| 2005/0143765 A1 | 6/2005 | Bachmann et al. |
| 2005/0143766 A1 | 6/2005 | Bachmann et al. |
| 2005/0177111 A1 | 8/2005 | Ozeri et al. |
| 2005/0183730 A1 | 8/2005 | Byrum |
| 2005/0192531 A1 | 9/2005 | Birk |
| 2005/0192601 A1 | 9/2005 | Demarais |
| 2005/0240155 A1 | 10/2005 | Conlon |
| 2005/0240156 A1 | 10/2005 | Conlon |
| 2005/0250979 A1 | 11/2005 | Coe |
| 2005/0251181 A1 | 11/2005 | Bachmann |

(56) References Cited

U.S. PATENT DOCUMENTS

| | | |
|---|---|---|
| 2005/0251182 A1 | 11/2005 | Bachmann |
| 2005/0277899 A1 | 12/2005 | Conlon et al. |
| 2005/0283041 A1 | 12/2005 | Egle |
| 2006/0009697 A1 | 1/2006 | Banet et al. |
| 2006/0074439 A1 | 4/2006 | Garner et al. |
| 2006/0079766 A1 | 4/2006 | Neer et al. |
| 2006/0079767 A1 | 4/2006 | Gibbs et al. |
| 2006/0149161 A1 | 7/2006 | Wilson et al. |
| 2006/0161186 A1 | 7/2006 | Hassler, Jr. et al. |
| 2006/0173238 A1 | 8/2006 | Starkebaum |
| 2006/0173424 A1 | 8/2006 | Conlon |
| 2006/0189888 A1 | 8/2006 | Hassler, Jr. |
| 2006/0199997 A1 | 9/2006 | Hassler, Jr. et al. |
| 2006/0211912 A1 | 9/2006 | Dlugos et al. |
| 2006/0235448 A1 | 10/2006 | Roslin et al. |
| 2006/0264762 A1 | 11/2006 | Starr |
| 2007/0001447 A1 | 1/2007 | Fennington, Jr. |
| 2007/0015954 A1 | 1/2007 | Dlugos |
| 2007/0015955 A1 | 1/2007 | Tsonton |
| 2007/0027356 A1 | 2/2007 | Ortiz |
| 2007/0106153 A1 | 5/2007 | Neer et al. |
| 2007/0156013 A1 | 7/2007 | Birk |
| 2007/0167672 A1 | 7/2007 | Dlugos et al. |
| 2007/0185462 A1 | 8/2007 | Byrum |
| 2007/0191717 A1 | 8/2007 | Rosen et al. |
| 2007/0218083 A1 | 9/2007 | Brooks |
| 2007/0235083 A1 | 10/2007 | Dlugos et al. |
| 2007/0250085 A1 | 10/2007 | Bachmann et al. |
| 2007/0250086 A1 | 10/2007 | Wiley et al. |
| 2007/0255336 A1 | 11/2007 | Herbert et al. |
| 2007/0265645 A1 | 11/2007 | Birk et al. |
| 2008/0009680 A1 | 1/2008 | Hassler, Jr. |
| 2008/0015406 A1 | 1/2008 | Dlugos |
| 2008/0027469 A1 | 1/2008 | Bachmann |
| 2008/0097496 A1 | 4/2008 | Chang et al. |
| 2008/0108862 A1 | 5/2008 | Jordan et al. |
| 2008/0108896 A1 | 5/2008 | Gibbs et al. |
| 2008/0108941 A1 | 5/2008 | Neer |
| 2008/0108943 A1 | 5/2008 | Wagner |
| 2008/0114302 A1 | 5/2008 | Neer |
| 2008/0221598 A1 | 9/2008 | Dlugos |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0294097 A1 | 11/2008 | Kim et al. |
| 2008/0306443 A1 | 12/2008 | Neer et al. |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0163803 A1 | 6/2009 | Neer et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0188494 A1 | 7/2009 | Imai et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216193 A1 | 8/2009 | Schriver et al. |
| 2009/0216255 A1 | 8/2009 | Coe et al. |
| 2009/0222031 A1 | 9/2009 | Axelsson |
| 2009/0222065 A1 | 9/2009 | Dlugos, Jr. et al. |
| 2009/0228072 A1 | 9/2009 | Coe et al. |
| 2009/0241677 A1 | 10/2009 | Klees et al. |
| 2009/0270759 A1 | 10/2009 | Wilson et al. |
| 2009/0270904 A1 | 10/2009 | Birk et al. |
| 2009/0306462 A1 | 12/2009 | Lechner |
| 2009/0312635 A1 | 12/2009 | Shimchuk et al. |
| 2010/0010291 A1 | 1/2010 | Birk et al. |
| 2010/0087843 A1 | 4/2010 | Bertolote et al. |
| 2010/0099945 A1 | 4/2010 | Birk et al. |
| 2010/0100079 A1 | 4/2010 | Berkcan et al. |
| 2010/0152532 A1 | 6/2010 | Marcotte |
| 2010/0185049 A1 | 7/2010 | Birk et al. |
| 2010/0191271 A1 | 7/2010 | Lau et al. |
| 2010/0228080 A1 | 9/2010 | Tavori et al. |
| 2010/0249803 A1 | 9/2010 | Griffiths |
| 2010/0280310 A1 | 11/2010 | Raven |
| 2010/0305397 A1 | 12/2010 | Birk et al. |
| 2010/0324358 A1 | 12/2010 | Birk et al. |
| 2010/0324359 A1 | 12/2010 | Birk et al. |
| 2011/0130626 A1 | 6/2011 | Hassler, Jr. et al. |

FOREIGN PATENT DOCUMENTS

| | | |
|---|---|---|
| DE | 19802615 | 8/1999 |
| EP | 1396242 | 3/2004 |
| EP | 1396243 | 3/2004 |
| EP | 1547549 | 6/2005 |
| EP | 1600183 | 11/2005 |
| EP | 1602346 | 12/2005 |
| EP | 1704833 | 9/2006 |
| EP | 1736123 | 12/2006 |
| EP | 1949875 | 7/2008 |
| EP | 1967168 | 9/2008 |
| EP | 1992316 | 11/2008 |
| EP | 2095797 | 9/2009 |
| EP | 2095798 | 9/2009 |
| FR | 2797181 | 2/2001 |
| FR | 2823663 | 10/2002 |
| FR | 2855744 | 12/2004 |
| FR | 2921822 | 4/2009 |
| JP | 2005-334658 | 12/2005 |
| WO | WO 00/09047 | 2/2000 |
| WO | WO 00/15158 | 3/2000 |
| WO | WO 01/10359 | 2/2001 |
| WO | WO 01/12078 | 2/2001 |
| WO | WO 01/47575 | 7/2001 |
| WO | WO 01/49245 | 7/2001 |
| WO | WO 03/105732 | 12/2003 |
| WO | WO 2004/019671 | 3/2004 |
| WO | WO 2005/009305 | 2/2005 |
| WO | WO 2009/023247 | 2/2009 |

SYRINGE-BASED LEAK DETECTION SYSTEM

FIELD

The present invention generally relates to medical systems, apparatuses and uses thereof for treating obesity and/or obesity-related diseases, and specifically relates to a syringe-based leak detection system directed to detecting a leak in a gastric banding system.

BACKGROUND

Adjustable gastric banding apparatus have provided an effective and substantially less invasive alternative to gastric bypass surgery and other conventional surgical weight loss procedures. Unlike gastric bypass procedures, gastric band apparatus are reversible and require no permanent modification to the gastrointestinal tract. In addition, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed around the stomach, such as around the cardia or upper portion of a patient's stomach thereby forming a stoma that restricts food's passage into a lower portion of the stomach. When the stoma is of an appropriate size that is restricted by the gastric band, the food held in the upper portion of the stomach may provide a feeling of satiety or fullness that discourages overeating. An example of a gastric banding system is disclosed in Roslin, et al., U.S. Patent Pub. No. 2006/0235448, the entire disclosure of which is incorporated herein by this specific reference.

However, accidents or certain actions by the patient (e.g., overeating despite the presence of a gastric band) may result in a leak in the gastric band. While a leak might not injure the patient, it may reduce the efficacy of the gastric band. Accordingly, it is desirable to quickly and accurately determine the presence of a leak in a gastric band so that the leak may be repaired or the gastric band replaced.

Some attempts have been made to detect the presence of a leak. For example, with reference to FIG. 1, Wheeler et al., U.S. Patent Pub. No. 2003/0213285 discloses a device for measuring leaks in a motor system. However, motor system detectors might not be appropriate for usage within a human body.

With reference to FIG. 2, Brugger et al., U.S. Patent Pub. No. 2003/0009123 discloses applying a vacuum and analyzing the fluid for bubbles. However, such a system might not have a high level of accuracy or indicate the degree of the leak.

With reference to FIG. 3, Dlugos et al., U.S. Patent Pub. No. 2008/0015406 discloses using external devices to display pressure measurements at a syringe. However, such systems may be inefficient or cumbersome to use with many different parts. In addition, the system of Dlugos is an analog system.

Accordingly, there remains a need for a method, apparatus and/or system for more effectively detecting and communicating the presence of a leak in a gastric banding system.

SUMMARY

This Summary is included as to introduce, in an abbreviated form, various topics to be elaborated upon below in the Detailed Description. This Summary is not intended to identify key or essential aspects of the claimed invention. This Summary is similarly not intended for use as an aid in determining the scope of the claims.

Generally described herein are leak detectors capable of detecting a leak present in a gastric banding system, which in one embodiment, may include a gastric band and a coupled access port.

In one embodiment, the leak detector (which may include a syringe, a leak sensing unit and a needle) may measure pressure decay within a gastric banding system after the needle penetrates the patient's skin and is inserted into an access port connected to the gastric band. The pressure decay may be interpreted to determine if a leak is present in the gastric banding system.

A leak detector according to an embodiment of the present invention may include a needle, a leak sensing unit and a syringe. The leak sensing unit may include a display, a pressure sensor and a timing unit. The leak sensing unit may track pressure changes over time to determine if a leak is present.

In one embodiment, data collected by the leak sensing unit may be analyzed to determine the presence of a leak. For example, any number of different leak detection methods may be utilized including, but not limited to, a two-point difference equation, derivatives, and/or determination of the timing of pressure-related events.

In one embodiment, the measurement system and the display may be digital in nature to provide the physician with a clear and accurate result.

BRIEF DESCRIPTION OF THE DRAWINGS

The features, obstacles, and advantages of the present invention will become more apparent from the detailed description set forth below when taken in conjunction with the drawings. The drawings might not be drawn to scale. That is, certain embodiments, components, etc. may be exaggerated to clarify certain aspects of the drawings.

DETAILED DESCRIPTION

Apparatuses, systems and/or methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers may be re-used to indicate correspondence between referenced elements.

The present invention generally relates to leak detectors for detecting a leak within a gastric banding system. A leak may result in allowing saline or other fill materials to flow out of the gastric banding system, thereby decreasing the efficacy of the gastric banding system.

Figure 1:
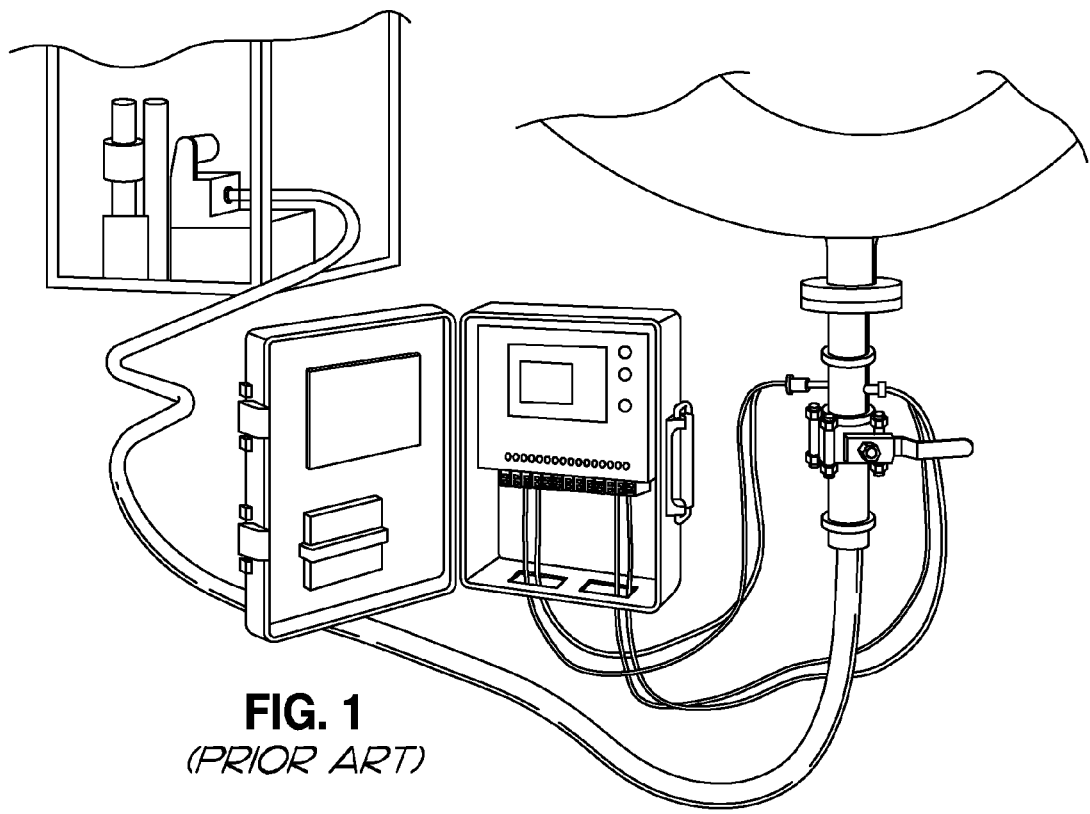
FIG. 1 illustrates a prior art system of a leak detecting device for motor systems.
Figure 2:
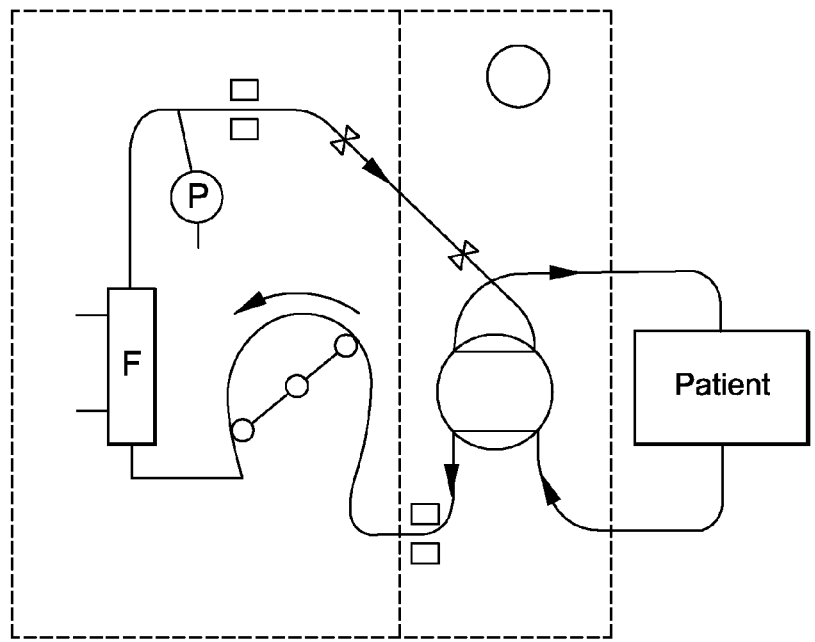
FIG. 2 illustrates a prior art system that checks for leaks in a medical device by using a vacuum and analyzing the fluid for air bubbles.
Figure 3:
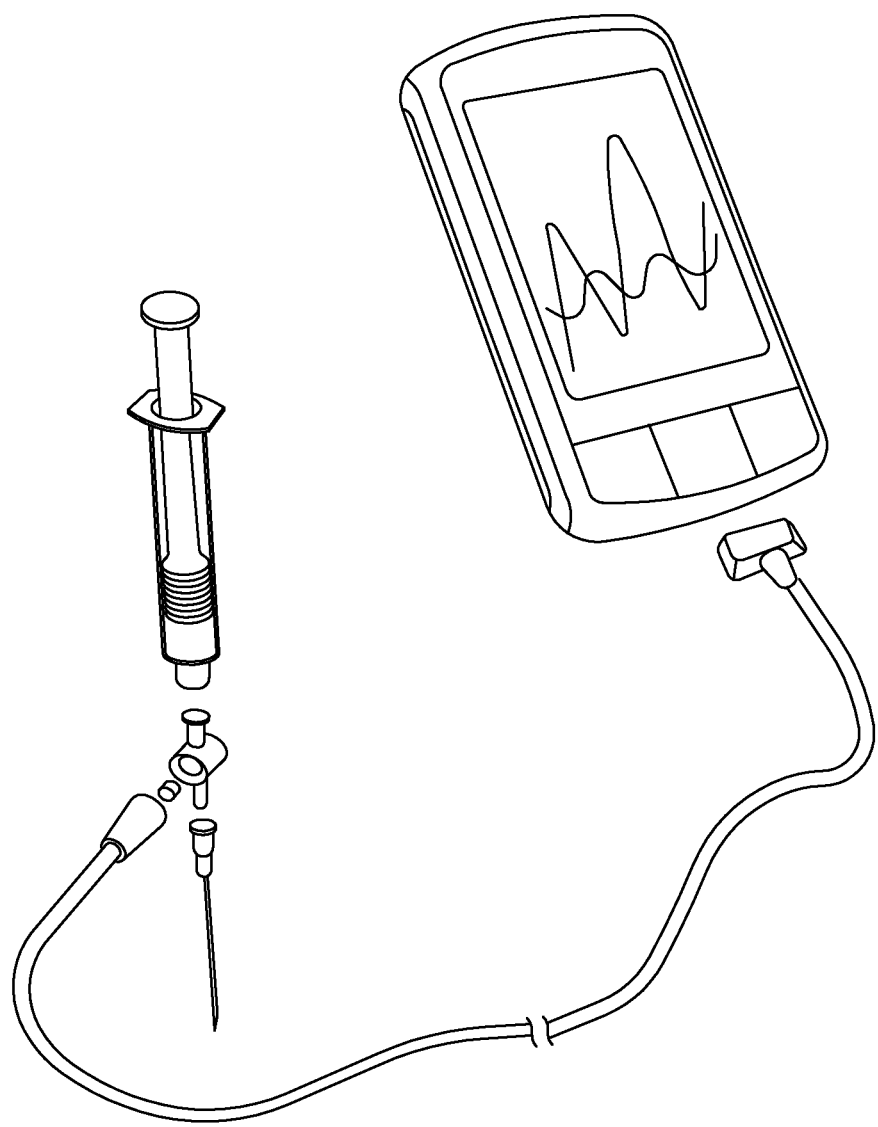
FIG. 3 illustrates a prior art system that uses external devices to display pressure measurements taken at a syringe.
Figure 4A:
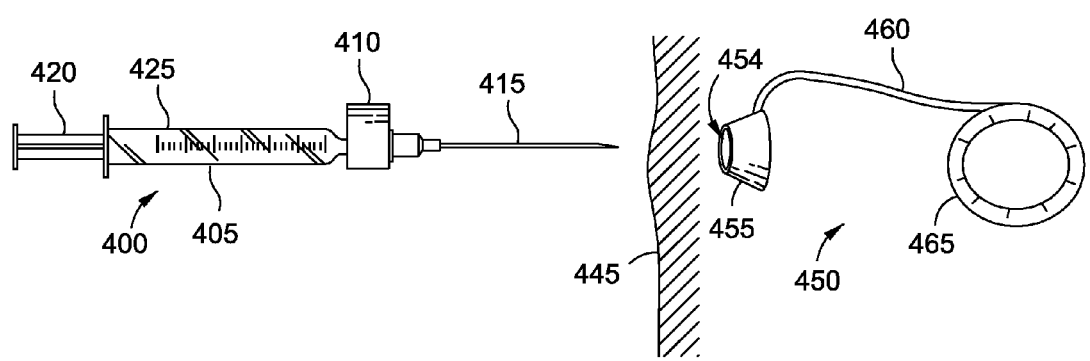
FIG. 4A illustrates a leak detection system for usage with an access port of a gastric banding system in accordance with one or more embodiments described herein.

Turning to FIG. 4A, a leak detector 400 is illustrated proximate to the location of an implanted gastric banding system 450 (e.g., near an esophageal-gastric junction of a patient). As shown, the leak detector 400 may include a syringe 405 with a plunger 420 and a barrel 425. The syringe 405 may be coupled to a leak sensing unit 410 and a needle 415. The needle 415 is intended to penetrate a patient's skin 445 and enter a septum 454 of an access port 455. When the plunger 420 is pressed into the barrel 425, fluid within the barrel 425 may be transferred through the needle 415, through the access port 455, and into a gastric band 465. Conversely, when the plunger 420 is pulled away from the barrel 425, fluid from the gastric banding system 450 may be transferred into the barrel 425 of the syringe 405. In this operational configuration, a fluid path between the syringe 405 of the leak detector 400 and the various components of the gastric banding system 450 is established when the needle 415 is inserted into the access port 455. Furthermore, assuming no leak is present, a closed system (comprising the gastric band 465, a tube 460, the access port 455, the needle 415, the leak sensing unit 410 and the syringe 405) may be achieved.

Figure 4B:
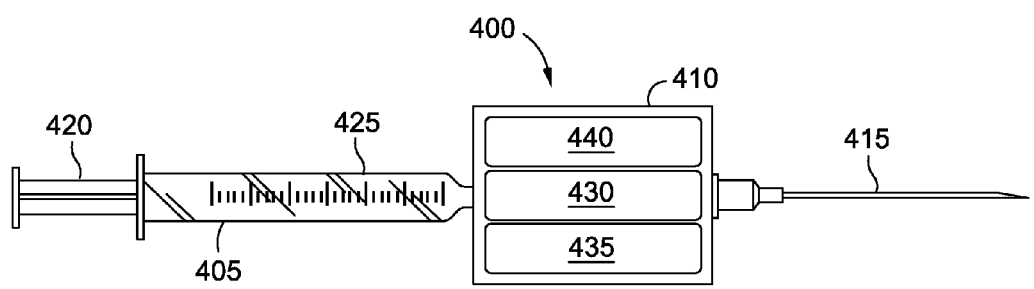
FIG. 4B illustrates a leak detection system including a syringe, a leak sensing unit and a needle in accordance with one or more embodiments described herein.

FIG. 4B illustrates the leak detector 400 in greater detail. For example, the leak sensing unit 410 may be disposed between the plunger 420 and the needle 415 (e.g., adjacent or within the barrel 425) and may include a pressure sensor 430, a timing unit 435 and a display 440.

The pressure sensor 430 may be configured to measure, sense or detect a pressure level within the syringe 405 or the gastric banding system 450 when, for example, the needle 415 is inserted into the access port 455 of the gastric banding system 450.

The timing unit 435 may be a clock or other time measuring device for determining a period of time to be used in conjunction with the pressure measurements to determine whether a leak is present and/or a magnitude of the leak. In one embodiment, the timing unit 435 may be a timer for counting and relaying counting information used by a processor 470 (shown infra in FIG. 4C).

The display 440 may be an LCD screen, an LED screen, or any other type of medium configured to visually output information. The display 440 may be configured to output the pressure-time information and/or any information derived or calculated therefrom. The display 440 may be located on the leak detector 400 as shown in FIG. 4B, or in other embodiments, may be located remotely. When a remote display (not shown) is used, the pressure/time information to be outputted may be transmitted via cable or wireless communication. The display 440 may further have speakers (not shown) which may alternatively and/or redundantly convey the same pressure/time information.

Figure 4C:
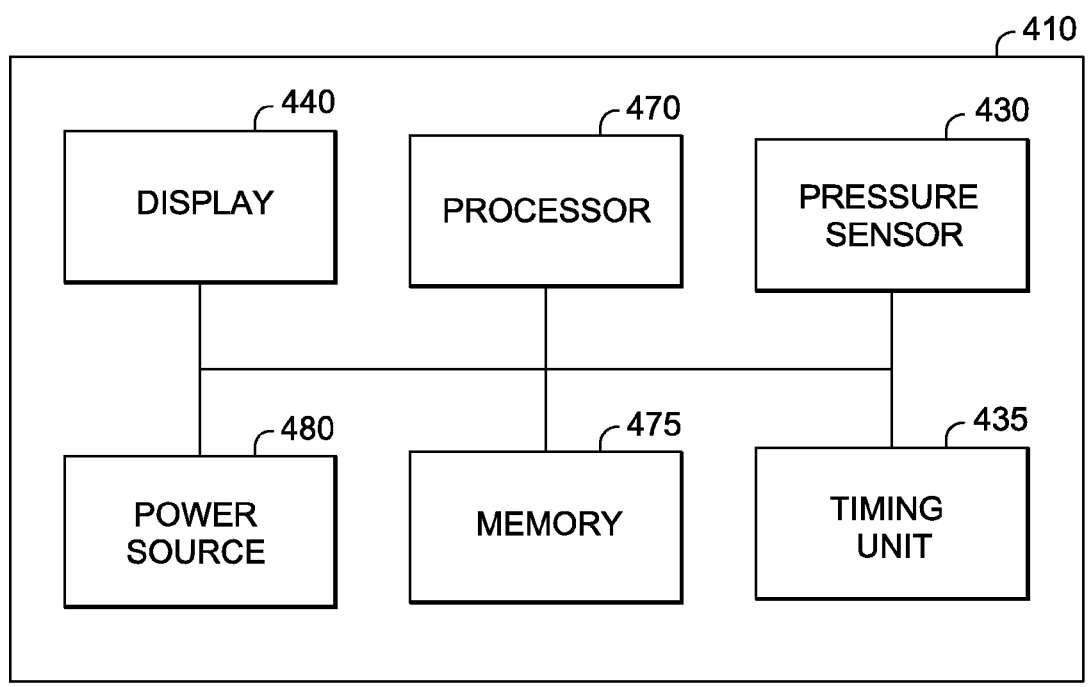
FIG. 4C illustrates a block diagram of the leak sensing unit in accordance with one or more embodiments described herein.
Figure 7A:
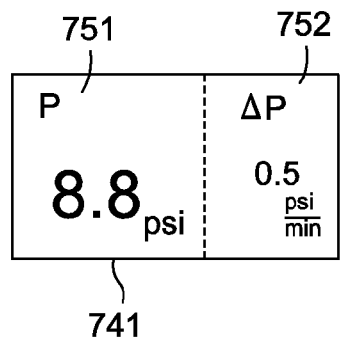
FIG. 7A illustrates a digital display for displaying pressure levels and/or pressure-time differences in accordance with one or more embodiments described herein.
Figure 7B:
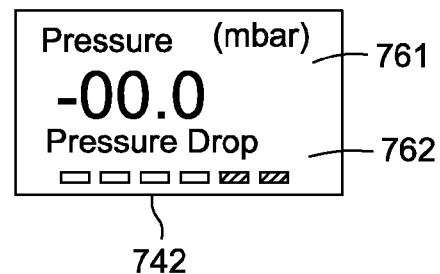
FIG. 7B illustrates an alternative digital display for displaying pressure levels and/or pressure-time differences in accordance with one or more embodiments described herein.
Figure 7C:
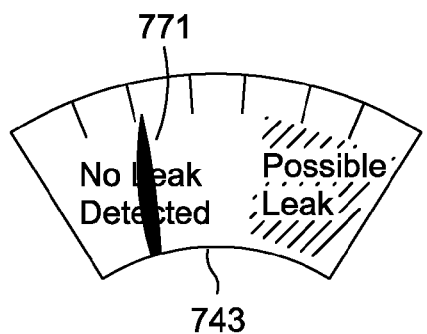
FIG. 7C illustrates a leak reporting display gauge for reporting the presence of a possible leak in accordance with one or more embodiments described herein.

FIG. 4C illustrates a block diagram of the leak sensing unit 410. The leak sensing unit 410 may include a pressure sensor 430 in fluid communication with a syringe (e.g., the syringe 405) and/or the gastric band 465. In one embodiment, the pressure sensor 430 may be coupled to one or more components such as the timing unit 435, the display 440, the processor 470, a memory 475 and a power source 480. The pressure sensor 430 may be a resistive sensor, a capacitive sensor, a piezoelectric sensor or some other sensor so long as the pressure sensor 430 is configured to measure, sense or detect a pressure level within the syringe 405 or the gastric banding system 450. The timing unit 435 may be integrated with the processor 470 or may be a separate component for measuring a period of time (e.g., a period of time when pressure measurements are to be obtained from the pressure sensor 430). The processor 470 may be configured to execute instructions stored in the physical memory 475 (e.g., a RAM, ROM, Flash, Hard Drive and/or any other tangible, non-transitory storage device storing computer readable instructions executable by the processor 470). The processor 470 may further provide instructions to the timing unit 435 and/or request and/or retrieve timing data from the timing unit 435. The processor 470 may also perform calculations, derivatives, and the like related to pressure decay information and/or leak detection. Similarly, the processor 470 may further provide instructions to the pressure sensor 430 and/or may request and/or retrieve pressure measurement data from the pressure sensor 430. In addition to storing instructions, the memory 475 may store any results generated from the pressure sensor 430, the timing unit 435 and/or the processor 470. The display 440 may display any information measured, manipulated and/or calculated by the pressure sensor 430, the timing unit 435, and/or the processor 470. In addition, the display 440 may further display any information stored in the memory 475. The display 440 may include several display modes selectable by the physician. Some embodiments are illustrated in FIGS. 7A-7C, infra.

The power source 480 may be a battery and may be coupled to the above described components to supply power thereto. However, other power sources may be utilized as well.

In one embodiment, the leak detector 400 may further include a lever (not shown) which may be switched to disconnect the hydraulic connection between the syringe 405 and the leak sensing unit 410. By isolating the syringe 405 from the gastric banding system 450, accuracy of the pressure readings may be improved. In other words, in some embodiments, the leak sensing unit 410 may operate independently of the syringe 405 during a leak detection operation after the fluid has been injected by the syringe 405.

Components of the leak detector 400 having been described, attention will now be turned to its operations.

Figure 5:
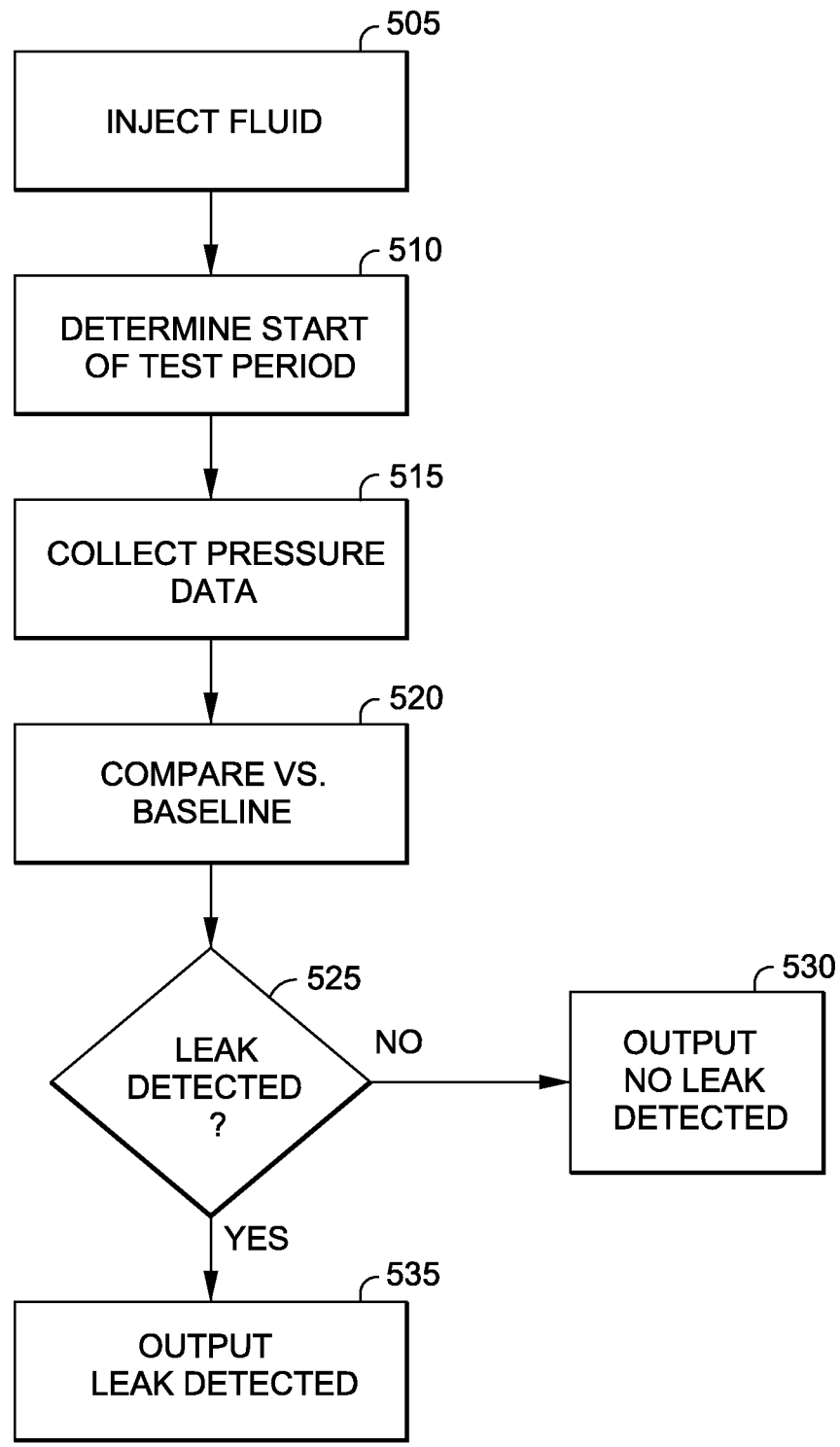
FIG. 5 illustrates a flow chart of a method of determining a leak within a gastric banding system in accordance with one or more embodiments described herein.

FIG. 5 is a flow chart of a method of detecting a leak within the gastric banding system 450. For example, at step 505, the leak test may begin with an injection of a known amount of fluid by the syringe 405 through the needle 415 and into the access port 455 of the gastric banding system 450 implanted inside the patient, thereby raising the pressure within the gastric banding system 450.

After sufficient time has passed to allow the gastric banding system 450 to stabilize, the pressure within the gastric banding system 450 may begin to drop. At step 510, the pressure sensor 430 may determine the initiation of the pressure drop. Alternatively and/or in addition, the timing unit 435 may be used to determine the initiation of the pressure drop by counting the time passed since the injection of the fluid and comparing it to an estimated time period when the pressure of the gastric banding system 450 typically begins to drop after injection of the fluid.

At step 515, pressure data may be collected by using the pressure sensor 430 over a predetermined time period. At step 520, the collected data may be compared to stored data. At step 525, the result of the comparison of step 520 may be analyzed. If a leak is detected (e.g., the pressure data results in pressure readings below a certain threshold thereby implying a leak), the process may move to step 535 where the presence of the leak is outputted to the physician via the display 440. However, if a leak is not detected at step 525 (e.g., the pressure data results in relatively high pressure readings above a certain threshold thereby implying proper gastric banding system 450 behavior), the process may move to step 530 where an indication of proper gastric banding system 450 behavior is outputted to the physician via the display 440. Other methods of pressure data analysis may be performed at step 520.

Figure 6:
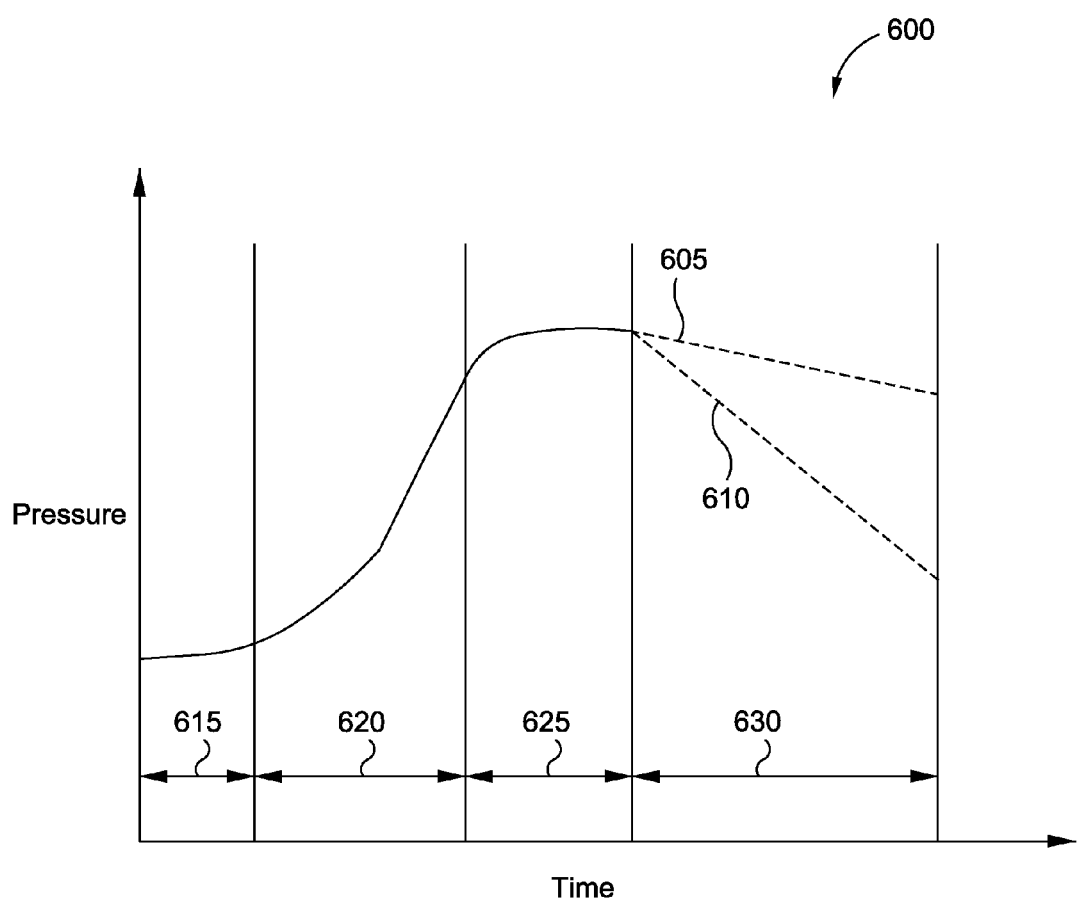
FIG. 6 illustrates pressure-decay curves related to the determination of a leak within a gastric banding system in accordance with one or more embodiments described herein.

For example, in one embodiment, pressure-decay curves may be used to determine the presence of a leak within the gastric banding system 450. FIG. 6 illustrates a graph 600 having pressure-decay curves related to the determination of a leak within the gastric banding system 450 of FIG. 4. As shown in FIG. 6, prior to any testing for leaks, the pressure within the gastric banding system 450 may be as shown for a time period 615. As the testing process begins, the pressure within the gastric banding system 450 may increase as shown by time period 620 when a known amount of fluid is injected into the gastric banding system 450 by the syringe 405.

A predetermined period of time (e.g., the time period 625) may be observed as a stabilization period where the pressure within the gastric banding system 450 may remain relatively constant. The pressure sensor 430 may be utilized to determine the end of the stabilization period (e.g., when the pressure begins to drop) and the timing unit 435 may be initialized or triggered to begin counting the stabilization period (e.g., time period 625). At the completion of the stabilization period (e.g., at the end of the time period 625), pressure data may be measured and collected by the pressure sensor 430 during a time period 630 as determined by the timing unit 435. The time period 630 may be a "test period" where pressure data is obtained at certain time intervals or continuously. Once the pressure data is obtained by the pressure sensor 435, analysis of whether a leak exists in the gastric banding system 450 may be performed. For example, the pressure data obtained by the pressure sensor 430 may be compared to a "no leak detected curve" 605 by the processor 470. If the pressure data is within a predetermined error range (e.g., 0-5%), a differential threshold is not crossed and the leak test ends with a result of "no leak detected" as outputted to the physician via the display 440. However, if the pressure data exceeds the differential threshold (e.g., closer to a "leak detected curve" 610 than the "no leak detected curve" 605) as determined by the processor 470, the leak test ends with a result of "leak detected" as outputted to the physician via the display 440. The "no leak curve" 605 may be based upon the premise that the gastric banding system 450 without a leak will exhibit a slow pressure drop or pressure decay as the materials relax or creep. In contrast, a "leak detected curve" 610 is indicative of a leak within the gastric banding system 450 and may exhibit a quicker pressure drop or pressure decay. Accordingly, comparing the rate of pressure decay, the leak detector 400 may be used to diagnose whether the gastric banding system 450 is leaking.

In one embodiment, a two-point difference equation may be used: $\Delta P$ (psi/minute)$=(P_2-P_1)/(T_2-T_1)$, where $\Delta P$ is a pressure difference, $P_2$ is a pressure (psi) at the end of the test period 630, $P_1$ is a pressure (psi) at the beginning of the test period 630, $T_2$ is a time (in minutes) at the end of the test period 630, and $T_1$ is a time (in minutes) at the beginning of the test period 630.

In one embodiment, a percentage pressure drop may be used: $\Delta P$ (% psi/minute)$=2(P_2-P_1)/[(P_2+P_1)(T_2-T_1)]$, where $\Delta P$ is a percentage difference, $P_2$ is a pressure (psi) at the end of the test period 630, $P_1$ is a pressure (psi) at the beginning of the test period 630, $T_2$ is a time (in minutes) at the end of the test period 630, and $T_1$ is a time (in minutes) at the beginning of the test period 630.

While these two examples may utilize the scenario where $P_2$ is a pressure (psi) at the end of the test period 630, $P_1$ is a pressure (psi) at the beginning of the test period 630, $T_2$ is a time (in minutes) at the end of the test period 630, and $T_1$ is a time (in minutes) at the beginning of the test period 630, other pressure samples at other intervals within the test period 630 may be used. In addition, other units of pressure (e.g., mbar, mmHG, cmH$_2$O, psia, psig, pascals) and other units of time (e.g., milliseconds, seconds, hours, days) may be used.

Further methods of pressure data analysis may be utilized, which for example, involve derivatives. When a set of pressure and time data is collected during test period 630, the set of data may be approximated by a curve (not shown). The curve may be analyzed, and a corresponding first and/or second derivative may be calculated to determine the rate of pressure drop.

Once the rate of the pressure drop is calculated, it may be outputted as a raw number or analyzed by applying an algorithm in order to display a leak warning (e.g., a red light indicating "leak detected"). In one embodiment, the raw number may be compared with predetermined "acceptable leak rates". In one embodiment, the processor 470 may be used to compare the measured pressure rates with a set of data stored in memory 475 to determine whether the predetermined "acceptable leak rates" has been passed.

Alternatively and/or in addition, in one embodiment, calculating the time elapsed between pressure-related events may be measured to determine pressure loss rate without ever measuring the pressure. Such a method may be used as a redundant leak detecting system (e.g., to confirm that the pressure sensor 430 is working properly).

FIGS. 7A-7C illustrate various examples of leak detector displays (e.g., as may be displayed on the display 440). FIG. 7A illustrates a digital display 741 having a pressure read-out 751 and a pressure difference read-out 752. FIG. 7B illustrates a digital display 742 having a pressure read-out 761 and a pressure drop bar portion 762. FIG. 7C illustrates a display gauge 743 with a needle 771 illustrating a leak detection result (e.g., "possible leak" or "no leak detected").

The displays 741, 742 and 743 may each be an embodiment of the display 440, and may be designed to continuously indicate the information related to pressure and/or leak detection. Alternatively, certain information may be used to trigger the display 440 (e.g., a display 440 may be in "sleep mode" and may automatically be awakened when detecting a pressure change over a predetermined threshold). In further embodiments, the leak detector 400 may temporarily disable the display 440 when pressure instabilities or fluctuations may imply inaccurate results or, alternatively, may display an error message.

While the embodiments herein have been described in relation to the gastric banding system 450 for clarity and ease of understanding, one skilled in the art will understand that the principles described herein are applicable to any gastric banding system incorporating any number of components whether described herein or not.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A leak sensing unit for determining a presence of a leak within a gastric band placed around a patient's stomach for the treatment of obesity, the leak sensing unit comprising:
    a pressure sensor for sensing a pressure level within the gastric band;
    a processor coupled to the pressure sensor for determining whether the sensed pressure level indicates a leak in the gastric band;
    a timing unit coupled to the processor, the timing unit for determining timing information used by the processor in determining whether the sensed pressure level indicates a leak in the gastric band;
    a memory coupled to the processor for storing the sensed pressure levels; and
    a digital display coupled to the processor for displaying information related to the sensed pressure level,
    wherein the pressure sensor, the processor, the timer, the memory, and the digital display are retained as a unit.

2. The leak sensing unit of claim 1 wherein the processor determines whether the sensed pressure level indicates a leak in the gastric band by solving a two-point difference equation for $\Delta P$, where $\Delta P=(P2-P1)/(T2-T1)$, and wherein P2 is a pressure at the end of a test period, P1 is a pressure at the beginning of the test period, T2 is a time at the end of the test period, and T1 is a time at the beginning of the test period.

3. The leak sensing unit of claim 1 wherein the processor determines whether the sensed pressure level indicates a leak in the gastric band by solving a pressure drop equation for $\Delta P$, where $\Delta P=2(P2-P1)/[(P2+P1)(T2-T1)]$, and wherein P2 is a pressure at the end of a test period, P1 is a pressure at the beginning of the test period, T2 is a time at the end of the test period, and T1 is a time at the beginning of the test period.

4. The leak sensing unit of claim 1 wherein the processor determines whether the sensed pressure level indicates a leak in the gastric band by comparing the sensed pressure level with a predetermined threshold.

5. The leak sensing unit of claim 1 wherein the timing unit is triggered in response to the sensed pressure level decreasing beyond a predetermined threshold.

6. The leak sensing unit of claim 1 wherein the digital display displays a numerical pressure reading in a first portion and a numerical rate of pressure change reading in a second portion.

7. The leak sensing unit of claim 1 wherein the digital display displays a numerical pressure reading in a first portion and a graphical pressure drop reading in a second portion.

8. The leak sensing unit of claim 1 wherein the digital display displays a graphical representation of a leak detector gauge with a needle.

9. The leak sensing unit of claim 1 wherein the pressure sensor is triggered when fluid is passed through the leak sensing unit into the gastric band.

10. A leak detector for determining a leak within a gastric banding system placed about the cardia of a patient's stomach for the treatment of obesity, the leak detector comprising:

a syringe having a plunger and a barrel;
a leak sensing unit fluidly coupled to the syringe, the leak sensing unit including:
   a pressure sensor for obtaining pressure readings within the gastric banding system,
   a processor coupled to the pressure sensor, the processor for interpreting whether the obtained pressure readings within the gastric banding system indicate a leak in the gastric banding system,
   a timer coupled to the processor, the timer for counting and relaying counting information used by the processor in interpreting whether the obtained pressure readings within the gastric banding system indicate a leak in the gastric banding system,
   a memory coupled to the processor for storing the obtained pressure readings, and
   a digital display coupled to the processor for displaying information related to the obtained pressure readings; and
a needle fluidly coupled to both the leak sensing unit and the syringe, the needle for establishing a fluid connection with an access port of the gastric banding system,
wherein the pressure sensor, the processor, the timer, the memory, and the digital display are retained as a unit in a location between the barrel and the needle.

11. The leak detector of claim 10 wherein the processor determines whether the obtained pressure readings indicate a leak in the gastric banding system by solving a two-point difference equation for $\Delta P$, where $\Delta P=(P2-P1)/(T2-T1)$, and wherein P2 is a pressure at the end of a test period, P1 is a pressure at the beginning of the test period, T2 is a time at the end of the test period, and T1 is a time at the beginning of the test period.

12. The leak detector of claim 10 wherein the processor determines whether the obtained pressure readings indicate a leak in the gastric banding system by solving a pressure drop equation for $\Delta P$, where $\Delta P=2(P2-P1)/[(P2+P1)(T2-T1)]$, and wherein P1 is a pressure at the end of a test period, P1 is a pressure at the beginning of the test period, T2 is a time at the end of the test period, and T1 is a time at the beginning of the test period.

13. The leak detector of claim 10 wherein the processor determines whether the obtained pressure readings indicate a leak in the gastric banding system by comparing the obtained pressure readings with a predetermined threshold.

14. The leak detector of claim 10 wherein the timer is triggered in response to the obtained pressure readings decreasing beyond a predetermined threshold.

15. The leak detector of claim 10 wherein the digital display displays a numerical pressure reading in a first portion and a numerical rate of pressure change in a second portion.

16. The leak detector of claim 10 wherein the digital display displays a numerical pressure reading in a first portion and a graphical pressure drop reading in a second portion.

17. The leak detector of claim 10 wherein the digital display displays a graphical representation of a leak detector gauge with a needle.

18. The leak detector of claim 10 wherein the pressure sensor is triggered to obtain pressure readings when fluid is passed through the leak sensing unit into the access port.

19. A leak detector for determining a leak within a gastric banding system placed about the cardia of a patient's stomach for the treatment of obesity, the leak detector comprising:
   a needle for establishing a fluid connection with an access port of the gastric banding system;
   a syringe having a plunger and a barrel, the syringe configured to hold fluid in the barrel, and further configured to transfer the fluid from the barrel to a gastric banding system through the needle; and
   a leak sensing unit disposed between the needle and the syringe, the leak sensing unit including:
      a pressure sensor for obtaining pressure data of the gastric banding system when the needle is inserted into the access port and after the fluid is transferred from the barrel to the gastric banding system,
      a processor coupled to the pressure sensor, the processor for interpreting whether the obtained pressure data of the gastric banding system indicate a leak in the gastric banding system,
      a timer coupled to the processor, the timer for counting and relaying counting information used by the processor in interpreting whether the obtained pressure data within the gastric banding system indicate a leak in the gastric banding system,
      a memory coupled to the processor for storing the obtained pressure data, and
      a digital display coupled to the processor for displaying information related to the obtained pressure data.

20. The leak detector of claim 19 wherein the processor determines whether the obtained pressure data indicate a leak in the gastric banding system by solving a two-point difference equation for $\Delta P$, where $\Delta P=(P2-P1)/(T2-T1)$, and wherein P2 is a pressure at the end of a test period, P1 is a pressure at the beginning of the test period, T2 is a time at the end of the test period, and T1 is a time at the beginning of the test period.

21. The leak detector of claim 19 wherein the processor determines whether the obtained pressure data indicate a leak in the gastric banding system by solving a pressure drop equation for $\Delta P$, where $\Delta P=2(P2-P1)/[(P2+P1)(T2-T1)]$, and wherein P2 is a pressure at the end of a test period, P1 is a pressure at the beginning of the test period, T2 is a time at the end of the test period, and T1 is a time at the beginning of the test period.

* * * * *